(12) United States Patent
Fernández et al.

(10) Patent No.: US 6,261,549 B1
(45) Date of Patent: Jul. 17, 2001

(54) HUMAN MESENCHYMAL STEM CELLS FROM PERIPHERAL BLOOD

(75) Inventors: Mireya Fernández; José J. Minguell, both of Santiago (CL)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/108,838

(22) Filed: Jul. 1, 1998

Related U.S. Application Data
(60) Provisional application No. 60/051,651, filed on Jul. 3, 1997.

(51) Int. Cl.[7] .......................... A61K 38/00; A61K 38/19

(52) U.S. Cl. .................. 424/85.1; 514/2; 514/12; 930/140

(58) Field of Search ................... 424/85.1, 85.2, 424/93.7; 514/2, 12; 530/350, 351; 930/140, 145

(56) References Cited

U.S. PATENT DOCUMENTS

| | | | |
|---|---|---|---|
| 5,199,942 | 4/1993 | Gillis | 604/4.01 |
| 5,486,359 | * 1/1996 | Caplan et al. | 424/93.7 |
| 5,612,211 | * 3/1997 | Wilson et al. | 435/378 |

OTHER PUBLICATIONS

Paul, in "Fundamental Immunology", Third Edition, Raven Press, New York, pp. 773, 774, and 788, 1993.*
Roitt et al., in Immunology, Third Edition, Mosby–Year Book Eurpoe Limited, pp. 8.14–8.15, 1993.*
Science, 284:143–147, 1999.*
Bensinger et al. Blood, 85:1655–1658, 1995.*
Fernandez et al. Bone Marrow Transplantation, 20:265–271, 1997.*
Brandt, J., et al., "Cytokine–dependent Long–Term Culture of Highly Enriched Precursors of Hematopoietic Progenitor Cells from Human Bone Marrow," *J. Clin. Invest.*, 86:932–941 (1990).
Chao, N.J., et al., "Granulocyte Colony–Stimulating Factor 'Mobilized' Peripheral Blood Progenitor Cells Accelerate Granulocyte and Platelet Recovery After High–Dose Chemotherapy," *Blood*, 81(8):2031–2035 (1993).
Dedhar, S., et al., "Human granulocyte–macrophage colony–stimulation factor active on a variety of cell types of nonhemopoietic origin," *Proc. Natl. Acad. Sci. USA*, 85:9253–9257 (1988).
Fernández, M. and Minguell, J.J., "Adhesive Interactions in the Hematopoietic System: Regulation by Cytokines," *Proc. Soc. Exp. Biol. Med.*, 313–323 (1996).
Goldman, J., "Peripheral Blood Stem Cells for Allografting," *Blood*, 85(6):1413–1415 (1995).

Gronthos, S., et al., "The STRO–1+ Fraction of Adult Human Bone Marrow Contains the Osteogenic Precursors," *Blood*, 84(12):4164–4173 (1994).
Klein, G., et al., "Collagen Type VI in the Human Bone Marrow Microenvironment: A Strong Cytoadhesive Component," *Blood*, 86(5):1740–1748 (1995).
Orazi, A., et al., "Recombinant Human Interleukin–3 and Recombinant Human Granulocyte–Macrophage Colony-Stimulating Factor Administered in Vivo After High–Dose Cyclophosphamide Cancer Chemotherapy: Effect on Hematopoieses and Microenvironment in Human Bone Marrow," *Blood*, 79(10):2610–2619 (1992).
Ross, A.A., et al., "Detection and Viability of Tumor Cells in Peripheral Blood Stem Cell Collections From Breast Cancer Patients Using Immunocytochemical and Clonogenic Assay Techniques," *Blood*, 82(9):2605–2610 (1993).
Silva, M.R.G., et al., "Natural killer cell numbers anbd activity in mobilized peripheral blood stem cell grafts: Conditions for in vitro expansion," *Experimental Hematology*, 23:1676–1681 (1995).
Wilkens, B.S. and Jones, D.B., "Immunohistochemical characterization of intact stromal layers in long–term cultures of human bone marrow," *British Journal of Haematology*, 90:757–766 (1995).

* cited by examiner

*Primary Examiner*—Deborah J. R. Clark
*Assistant Examiner*—Janet M Kerr
(74) *Attorney, Agent, or Firm*—Elliot M. Olstein; Raymond J. Lillie

(57) ABSTRACT

Disclosed is a method for recovering peripheral blood containing a population of cells enhanced in human mesenchymal stem cells from an individual by (i) administering to said individual at least one growth factor and, thereafter, (ii) recovering peripheral blood from said individual. The growth factors preferably include G-CSF, GM-CSF and combinations thereof. Any of the known human growth factors or combinations thereof are suitable. Also disclosed is a method for recovering an isolated, culture-expanded population of human mesenchymal stem cells from the mesenchymal stem cell-enriched peripheral blood of an individual. Also disclosed is a method for preserving ex vivo an isolated, culture-expanded population of human mesenchymal stem cells from the mesenchymal stem cell-enriched peripheral blood. Also disclosed is a method for treating an individual with an isolated, culture-expanded population of human mesenchymal stem cells.

2 Claims, 7 Drawing Sheets

(5 of 7 Drawing Sheet(s) Filed in Color)

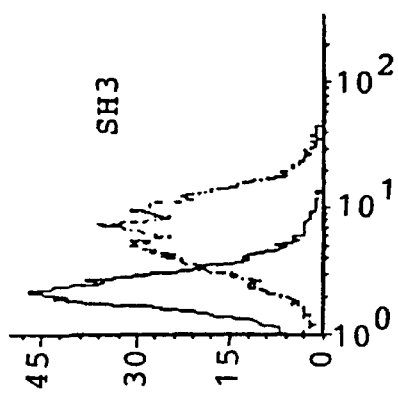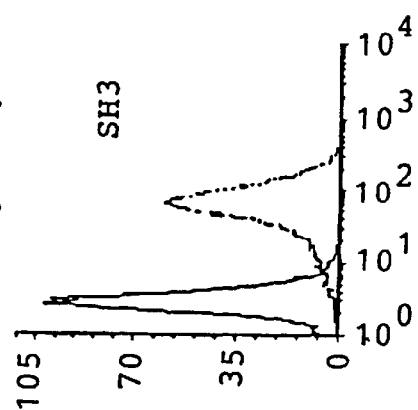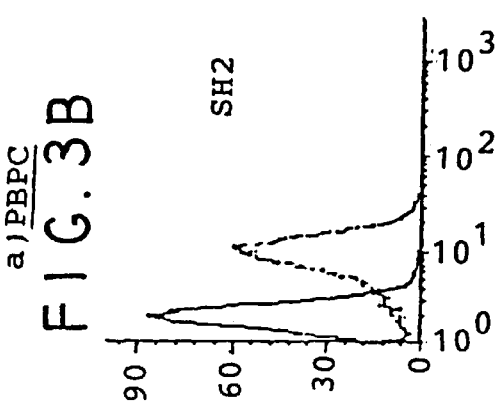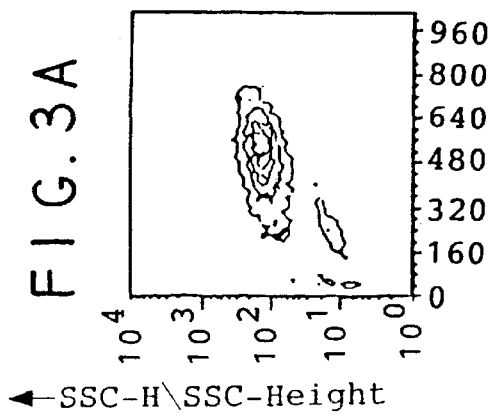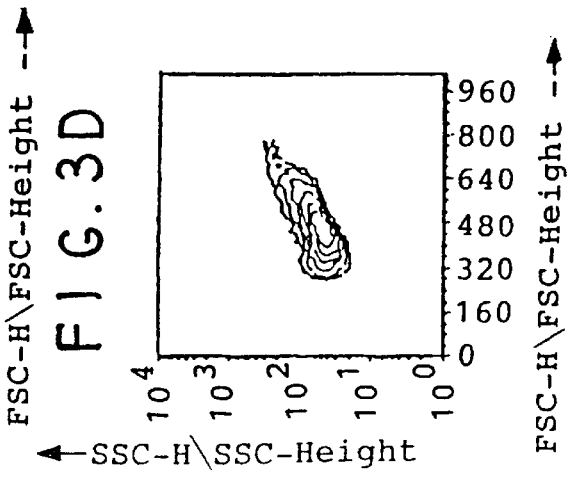

HUMAN MESENCHYMAL STEM CELLS FROM PERIPHERAL BLOOD

This application claims priority of U.S. provisional application serial No. 60/051,651, filed Jul. 3, 1997. This work was supported by grants FONDECYT-Chile (No.1950-238) and Fundacao Vitae-Brazil (No. B-11487/4B001). These may have created certain rights in the invention.

BACKGROUND OF THE INVENTION

Mesenchymal stem cells (MSCs) are the formative pluripotential blast cells found inter alia in bone marrow, blood, dermis and periosteum that are capable of differentiating into more than one specific type of mesenchymal or connective tissues (i.e. the tissues of the body that support the specialized elements; e.g. adipose, osseous, stroma, cartilaginous, elastic and fibrous connective tissues) depending upon various influences from bioactive factors, such as cytokines. Human mesenchymal stem cells (hMSCs) are reactive with certain monoclonal antibodies, known as SH2, SH3 and SH4. (See U.S. Pat. No. 5,486,359).

Hematopoietic stem cells (HSCs) are the formative pluripotential blast cells found inter alia in bone marrow and peripheral blood that are capable of differentiating into any of the specific types of hematopoietic or blood cells, such as erythrocytes, lymphocytes, macrophages and megakaryocytes. After mobilization of HSCs from bone marrow by administration of certain factors such as G-CSF and GM-CSF and subsequent recovery from peripheral blood, HSCs have also come to be referred to as peripheral blood progenitor cells (PBPCs). Human hematopoietic stem cells (hHSCs) and PBPCs are reactive with certain monoclonal antibodies which are now recognized as being specific for hematopoietic cells, for example, CD34.

Thus, hMSCs and hHSCs are readily distinguishable by their immunospecific profiles and, for the sake of clarity herein, will be referred to, for example, herein as $SH2^+$-$CD14^-$ hMSCs or $SH2^-$-$CD14^+$ hHSCs as needed.

Human hematopoietic stem cell (hHSC), or peripheral blood progenitor cell (PBPC), transplantation has become an accepted method for dose-intensification in the treatment of several neoplastic diseases.[1,2] Various procedures have been used for HHSC mobilization and removal from the circulation by apheresis. At present, most methods exploit the rebound in circulating progenitors that occurs after cytotoxic chemotherapy.[3] Together, the short-term administration of either GM-CSF or G-CSF, enhances the yield of hHSC, as measured by the number of $CD34^+$ cells [4,5,6] which, when used for autografting at $\geq 2.5 \times 10^6$ $CD34^+$ hHSC/kg recipient, ensures fast hematopoietic recovery.[4,5,6]

Several mechanisms seem to be involved in the growth factor-mediated release of marrow progenitor cells.[7] Among them, it appears that after exposure to G-CSF or GM-CSF, adhesion molecules are shed from the surface of marrow resident primitive multilineage cells, therefore allowing them to enter the circulation[5]. This concept, has been strengthened by several observations showing that growth factors (like G-CSF, GM-CSF, IL-3 and SCF) modulate the expression or function of several cytoadhesive molecules on the surface of hematopoietic progenitor cells.[8,9] In addition, reports cite that cytokines produce profound morphological and immunohistochemical changes in marrow stroma and in the contiguous extracellular matrix.[10,11]

SUMMARY OF THE INVENTION

Accordingly, the invention provides a method for obtaining human mesenchymal stem cells wherein the human mesenchymal stem cells are recovered from peripheral blood obtained from an individual. More particularly, the invention provides a method for recovering peripheral blood containing a population of cells enhanced in human mesenchymal stem cells from an individual which method comprises (i) administering to said individual at least one growth factor and, thereafter, (ii) recovering hMSCs from the peripheral blood from said individual. Growth factors which can be used are those, for example, which are known to mobilize hematopoietic stem cells. The growth factors preferably include G-CSF, GM-CSF and combinations thereof.

The invention further provides a method for recovering an isolated, culture-expanded population of human mesenchymal stem cells from the mesenchymal stem cell-enriched peripheral blood of an individual by (i) administering to said individual at least one growth factor; (ii) recovering mesenchymal stem cell-enriched peripheral blood from said individual; (iii) culturing the mesenchymal stem cell-enriched peripheral blood or a fraction thereof; and (iv) isolating a culture-expanded population of human mesenchymal stem cells from other cells in said mesenchymal stem cell-enriched peripheral blood. The steps of culturing and isolating can also be in the inverse order. That is, the mesenchymal stem cells can be isolated from the peripheral blood and then be culture-expanded. Approaches to such isolation include leucopheresis, density gradient fractionation, immunoselection and differential adhesion separation. The culture media can be chemically defined serum free media or can be a "complete medium", such as DMEM or DMEM-1 g containing serum. Suitable chemically defined serum free media are described in U.S. Ser. No. 08/464,599, filed Jun. 5, 1995, and "complete media" are described in U.S. Pat. No. 5,486,359, issued Jan. 23, 1996.

The invention further provides a method for preserving ex vivo an isolated, culture-expanded population of human mesenchymal stem cells from the mesenchymal stem cell-enriched peripheral blood of an individual by (i) administering to said individual at least one growth factor; (ii) recovering mesenchymal stem cell-enriched peripheral blood from said individual; (iii) culturing the mesenchymal stem cell-enriched peripheral blood; (iv) isolating a culture-expanded population of human mesenchymal stem cells from other cells in said mesenchymal stem cell-enriched peripheral blood; and (v) preserving the isolated, culture-expanded population of human mesenchymal stem cells. Preferably, the preservation is by cryopreservation.

The invention further provides a method for treating an individual in need of treatment with an isolated, culture-expanded population of human mesenchymal stem cells by (i) administering to said individual at least one growth factor; (ii) recovering mesenchymal stem cell-enriched peripheral blood from said individual; (iii) culturing the mesenchymal stem cell-enriched peripheral blood; (iv) isolating a culture-expanded population of human mesenchymal stem cells from other cells in said mesenchymal stem cell-enriched peripheral blood; and (v) administering said isolated, culture-expanded population of human mesenchymal stem cells to said individual. The cells can be administered by, for example, systemic infusion or local implantation into a site where de novo tissue generation is desired, such as by an open or arthroscopic procedure. The cells can be preserved prior to readministration.

BRIEF DESCRIPTION OF THE DRAWINGS

FIG. 1A. After culturing (10 days) low-density PBPCs in medium supplemented with 20% FCS, an adherent layer containing fibroblast-like cells, colonies and small round cells was generated (a). (×10).

FIG. 1B. Colonies are formed by fibroblast-like cells, large-flat round cells and small round cells dispersed or located on top of large-flat round cells (×100).

FIG. 1C. After 20 days in culture, an almost confluent adherent monolayer of fibroblast-like cells is visualized (×10).

Figure 2A:
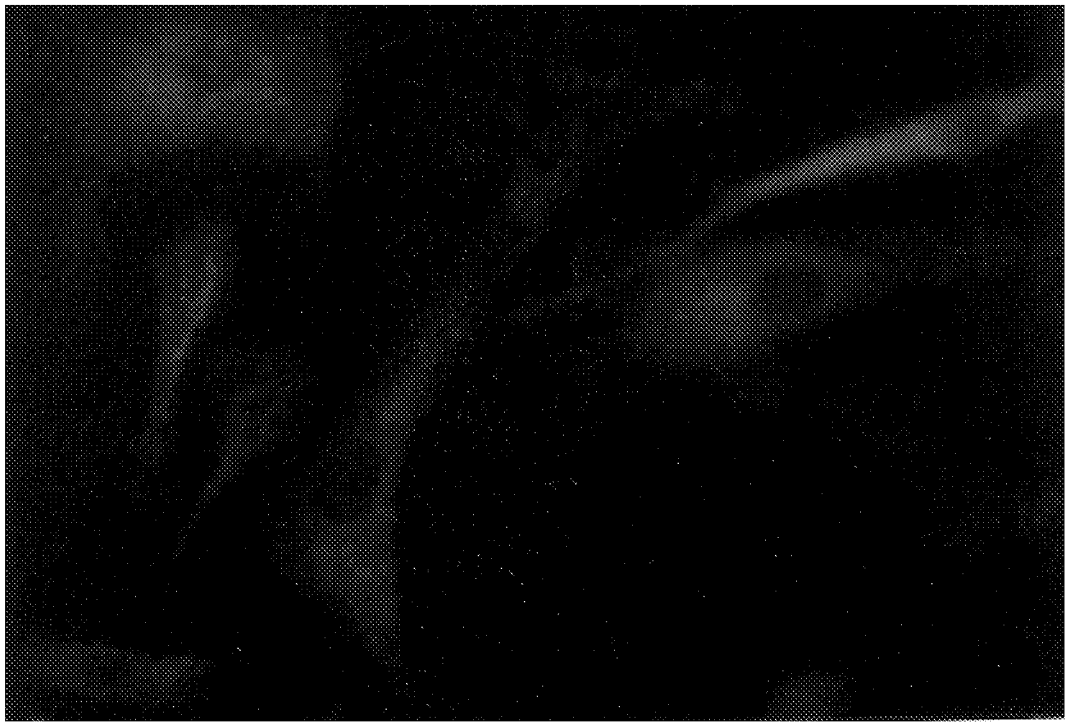
FIGS. 2A–2E. Immunostaining for fibronectin, collagen I, ICAM-1, VCAM-1 and mesenchymal antigen SH2 in cultures of stromal cells derived from mobilized PBPC harvests.
Figure 2B:
Figure 2C:
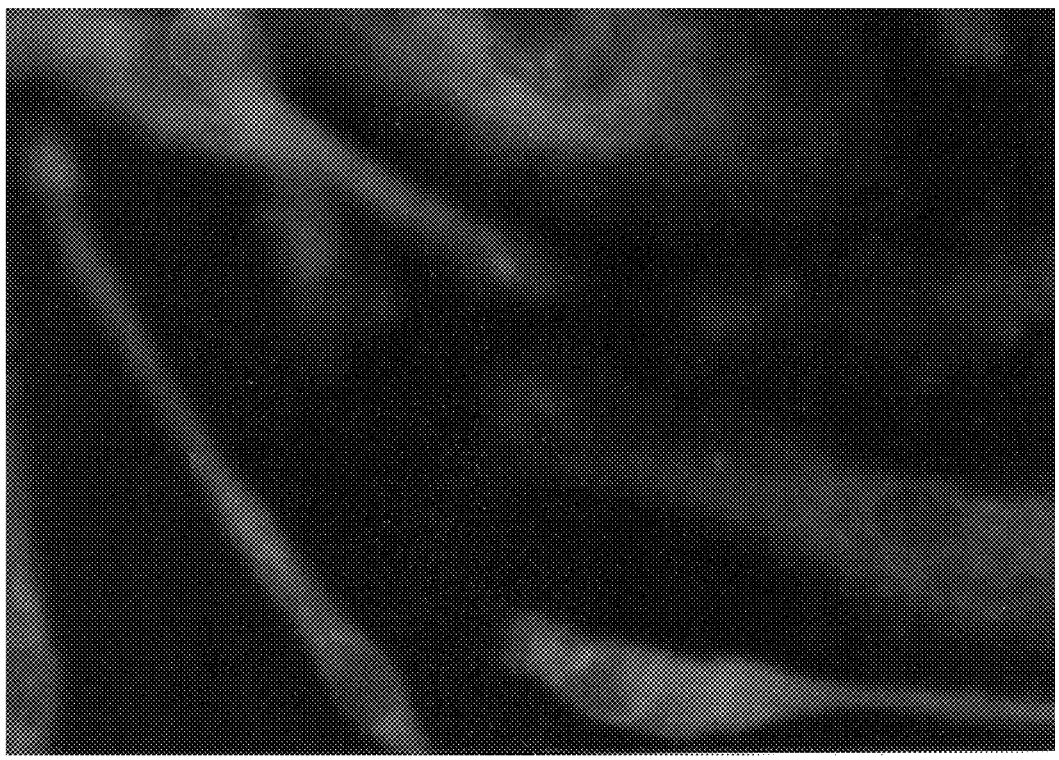
Figure 2D:
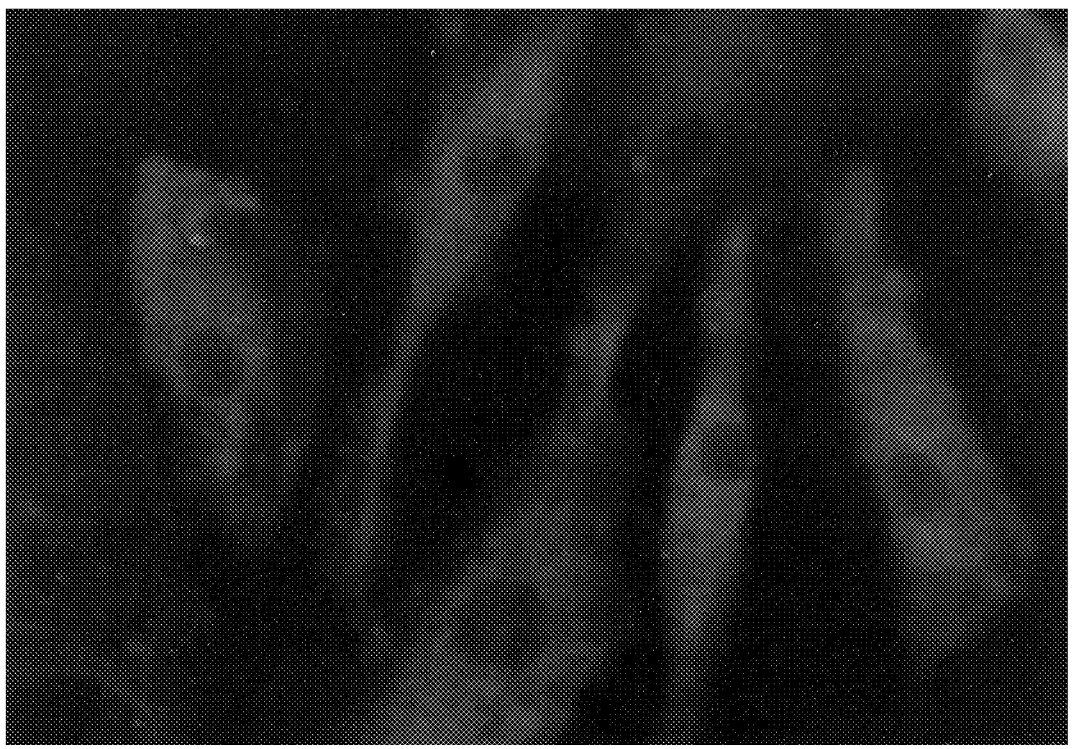
Figure 2E:

The micrographs show in situ immunofluorescence staining for fibronectin (FIG. 2A), collagen I (FIG. 2B), ICAM-1 (FIG. 2C), VCAM-1 (FIG. 2D) and mesenchymal antigen SH2 (FIG. 2E) Original magnification×40.

FIGS. 3A–3F. Representative FACScan histograms for the expression of mesenchymal stem cell-surface antigens.

Adherent cells from day 10-cultures of peripheral blood progenitor cells (PBPC) and bone marrow, were EDTA-released and analyzed for the expression of mesenchymal stem cell-associated surface antigens recognized by monoclonal antibodies SH-2 and SH-3. We show the scattergram of FSC vs. SSC for peripheral blood MSCs (FIG. 3A) and bone marrow MSCs (FIG. 3D) to allow gating of SH-2$^+$/CD14$^-$. The fluorescence profile on each of FIG. 3B, 3C, 3E and 3F shows the negative control without staining (left peak of each) and the positive control for stained cells (right peak of each).

Figure 4:
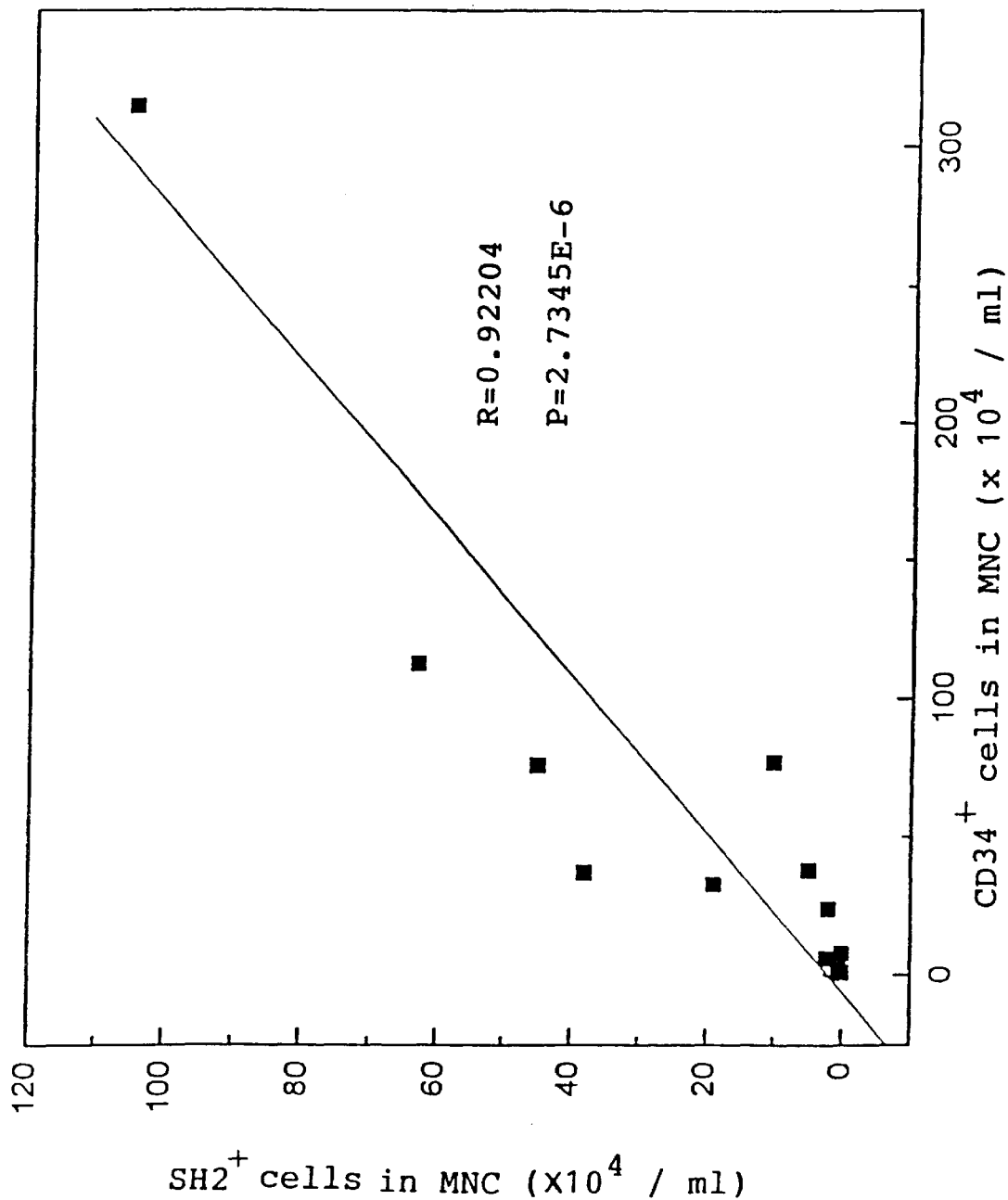

FIG. 4. Correlation between the number of CD34$^+$ and SH-2$^+$ cells in growth factor mobilized apheresis products.

Data from the apheresis products from 14 breast cancer patients were analyzed. CD34$^+$ and SH-2$^+$ numbers were normalized to $10^4$ mononuclear cells per ml of each harvest. The line represent the trend (correlation coefficient 0.92).

DETAILED DESCRIPTION OF PREFERRED EMBODIMENTS

The following are representative examples of cytokines which may be employed in the present invention: IL-1 may be employed in an amount effective to enrich the hMSC population in peripheral blood, generally, such amount is at least 20 pg/ml and need not exceed 1 ng/ml, preferably 1 ng/ml; IL-6 may be employed in an amount effective to enrich the hMSC population in peripheral blood, generally, such amount is at least 1 pg/ml and need not exceed 50 ng/ml preferably 10 ng/ml; IL-3 may be employed in an amount effective to enrich the hMSC population in peripheral blood, generally, such amount is at least 500 pg/ml and need not exceed 50 ng/ml, preferably 500 pg/ml; G-CSF may be employed in an amount effective to enrich the hMSC population in peripheral blood, and generally, such amount is at least 100 pg/ml and need not exceed 1 ng/ml, preferably 200 pg/ml. GM-CSF may be employed in an amount effective to enrich the hMSC population in peripheral blood, generally, such amount is at least 100 pg/ml and need not exceed 1 ng/ml, preferably 200 pg/ml; c-kit ligand may be employed in an amount effective to enrich the hMSC population in peripheral blood, generally, such amount is at least 1.0 ng/ml and need not exceed 500 ng/ml, preferably 100 ng/ml. Such cytokines may be employed alone or in combination with each other. Other cytokines, such as LIF and SCF, and combinations thereof may also be employed to mobilize hMSCs into peripheral blood.

The hMSCs recovered from peripheral blood in accordance with the present invention may be used in a variety of ways. For example, such hMSCs can be employed as part of cell replacement therapy. Specifically the expanded and cultivated hMSCs can be infused alone or added to bone marrow cells for bone marrow transplant procedures. Other applications, particularly orthopedic, are also contemplated. Such include, for example, the treatment of osteoarthritis, osteoporosis, traumatic or pathological conditions involving any of the connective tissues. It is also contemplated that exogenous genetic material can be introduced into the cells while ex vivo and that the cells be readministered as part of a gene therapy regimen. Genetic engineering of mesenchymal stem cells is discussed more fully in U.S. Pat. No. 5,591,625, issued Jan. 7, 1997.

The cells may be expanded, such as by the procedure taught in Caplan et al., U.S. Pat. No. 5,486,359 (issued Jan. 23, 1996), before or after freezing thereof. After chemotherapy, the expanded cells are reinfused into a patient by procedures known in the art.

The following examples are provided to further illustrate and describe the present invention; however, the scope of the present invention is not intended to be limited thereby.

EXAMPLE 1

Isolation of hMSCs from Peripheral Human Blood

In the present study, we detected the presence of hMSCs in growth factor-mobilized hHSC harvests from breast cancer patients. For this purpose, we used a procedure which included culturing of hMSCs and their quantification by flow cytometry using monoclonal antibodies raised against surface antigens expressed by marrow-derived hMSCs, i.e., SH2 and SH3. A similar approach has already been followed to demonstrate that marrow cells include the primitive mesenchymal stem cell.

Patient Population and hHSC Harvest Procedure

Fourteen female patients with histologically established, stage II-breast cancer with 10 or more involved axillary lymph nodes, were treated with (i) chemotherapy[6], and, then, (ii) with recombinant human G-CSF (Neupogen®, F. Hoffmann-La Roche Ltd., Basel, Switzerland) or GM-CSF (LeucomaxR, Schering Plough-Sandoz Pharma Ltd., Basel, Switzerland) at 5 µg/kg/d subcutaneously, one day after the end of chemotherapy. Thereafter a hHSC harvest was collected during marrow recovery as soon as a distinct population of CD34$^+$ ($\geq$10/1) was detectable in the peripheral blood, using a Haemonetics (Braintree, Mass.) V50 blood separator. An aliquot of hHSC harvest was counted and processed for morphological examination, CFU-GM assay[16] and CD34 content by direct immunofluorescence (see below). Another aliquot was set aside for culturing and phenotypic analysis of SH2$^+$ hMSCs. The hHSC harvests were volume-reduced by centrifugation, diluted in a mixture of autologous plasma and 10% DMSO, frozen in a rate-controlled freezer (Cryomed; Forma Scientific, Marietta, Ohio., USA) and cryopreserved in the vapor phase of liquid nitrogen until reinfused.

Bone Marrow Collection

Leftover material was obtained from heparinized bone marrow (BM) cells taken from normal individuals undergoing BM harvests for allogeneic transplantation. Cells in medium 199 containing 20 U/ml heparin were washed twice, resuspended in medium alone and used for culturing of marrow-derived hMSCs.

All procedures were done under the guidelines of the ethical committee of Clinica Las Condes. Informed consent was obtained from every patient.

Culturing of Peripheral Blood hHSCs and Marrow-derived hMSCs.

The hMSCs were cultured using previously reported methods.[12,13] Briefly, mononuclear cells from apheresis products and from BM harvests were density-separated by centrifugation on 1.077 g/cm$^3$ Ficoll-Hypaque (Sigma, St. Louis, Mo., USA). Low-density cells were suspended in α-MEM containing 20% fetal calf serum (FCS, Sigma, St.Louis, Mo., USA) and cultured in 35 mm Petri dishes at a concentration of $10^6$ cells/dish at 37° C. in a humidified atmosphere containing 5% $CO_2$. After 10 days in culture, with a change of medium at day 4, cells in the adherent layer were used for phenotypic analysis either in situ or after detachment of cells with 0.02% EDTA in phosphate-buffered saline.

Phenotypic Analysis.

Light-microscopic examination was performed on Wright-Giemsa stained cells either in the culture plate or in cytospin preparations of EDTA-detached cells. Histochemical staining was performed by standard protocols using diagnostic kits (Sigma) for Sudan Black, Periodic Acid-Schiff (PAS), a-naphthyl butyrate esterase, acid phosphatase and alkaline phosphatase.

For immunofluorescence studies, cells were processed with a fixation/permeabilization reagent (Cytoperm®, Serotech Ltd., Oxford, England) and labeled with appropriate free or FITC-conjugated monoclonal antibodies (see below) and read under ultraviolet illumination at 50 nm with a mercury gas lamp on a Nikon microscope. For flow cytometric analysis, EDTA-released cells or cells in the apheresis products were stained with either pure or FITC- or PE-conjugated monoclonal antibodies. Nonspecific isotype-matched antibodies were used to determine background fluorescence. Cells were analyzed on a FACScan flow cytometer (Becton Dickinson, BD) and data acquisition was performed with a FACScan Lysis II (BD) research software. Each measurement included at least 30,000 cells.

The following monoclonal antibodies were used: anti CD-45-FITC, anti-CD14-PE, anti-CD34-PE, were purchased from Becton Dickinson; anti collagen I, anti collagen III and anti fibronectin were from Sigma; anti collagen VI was from Gibco BRL (Grand Island, N.Y., USA); anti ICAM-1 (CD54) and anti VCAM-1 (CD106) were from R&D Systems (Minneapolis, Minn., USA). Control mouse $IgG_1$-PE, $IgG_1$-FITC, $IgG_{2a}$-PE and $F(ab')_2$-PE were purchased from Becton Dickinson. Monoclonal antibodies SH-2 ($IgG_1$) and SH-3 ($IgG_{2b}$) were kindly provided by Dr. A. I. Caplan (Case Western Reserve University, Cleveland, Ohio., USA) and by Osiris Therapeutics, Inc. (Baltimore, Md., USA). These antibodies recognize antigens on the cell surface of marrow-derived mesenchymal progenitor cells, but fail to react with marrow-derived hemopoietic cells as well as with the cell surface of osteoblasts or osteocytes[12,14,15].

RESULTS

Ex vivo generation of hMSCs from mobilized hHSC harvests.

Figure 1A:
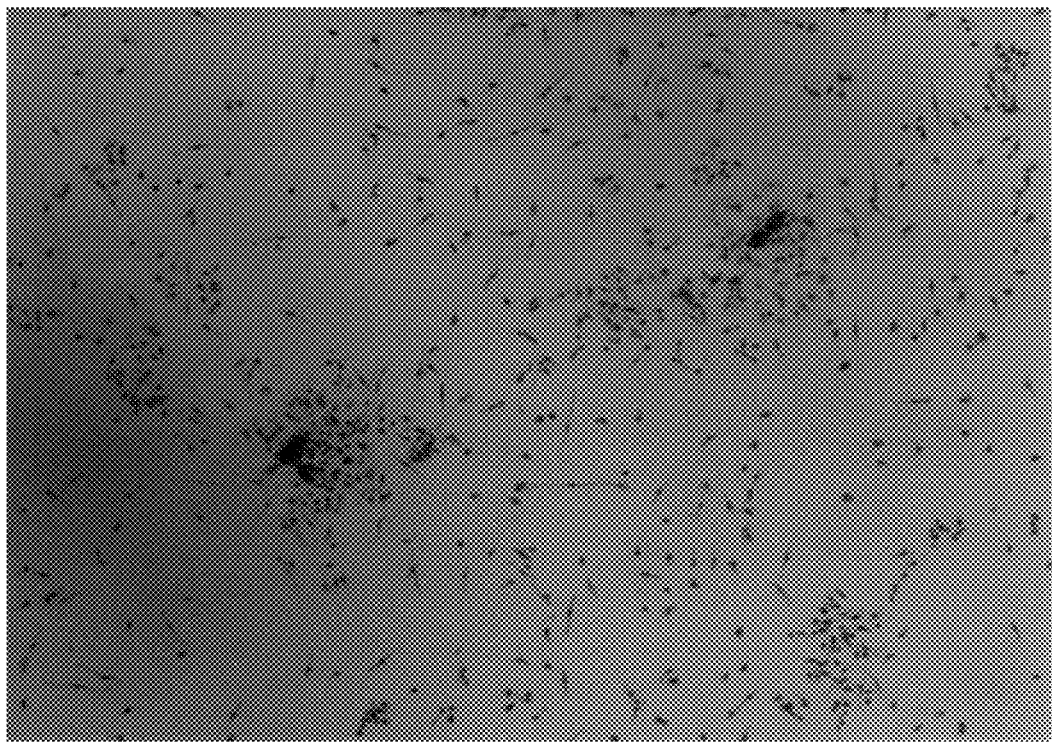
FIGS. 1A–1C. The claim of this patent contains at least one drawing executed in color. Phase contrast photomicrographs of cultured stromal cells from mobilized PBPC harvests.

Low-density mononuclear cells from hHSC harvests were grown in culture in the presence of FCS but in the absence of glucocorticoids or growth factors that favor the replication/differentiation of stromal and hematopoietic precursors, respectively.[15,16] After removing non-adherent cells by replacing the medium (day 4 of culture), a small portion of attached nucleated cells were visualized in the culture plate, which by day 10 of culture developed into an adherent layer containing abundant dispersed fibroblast-like cells and several large colonies (FIG. 1A).

Figure 1B:
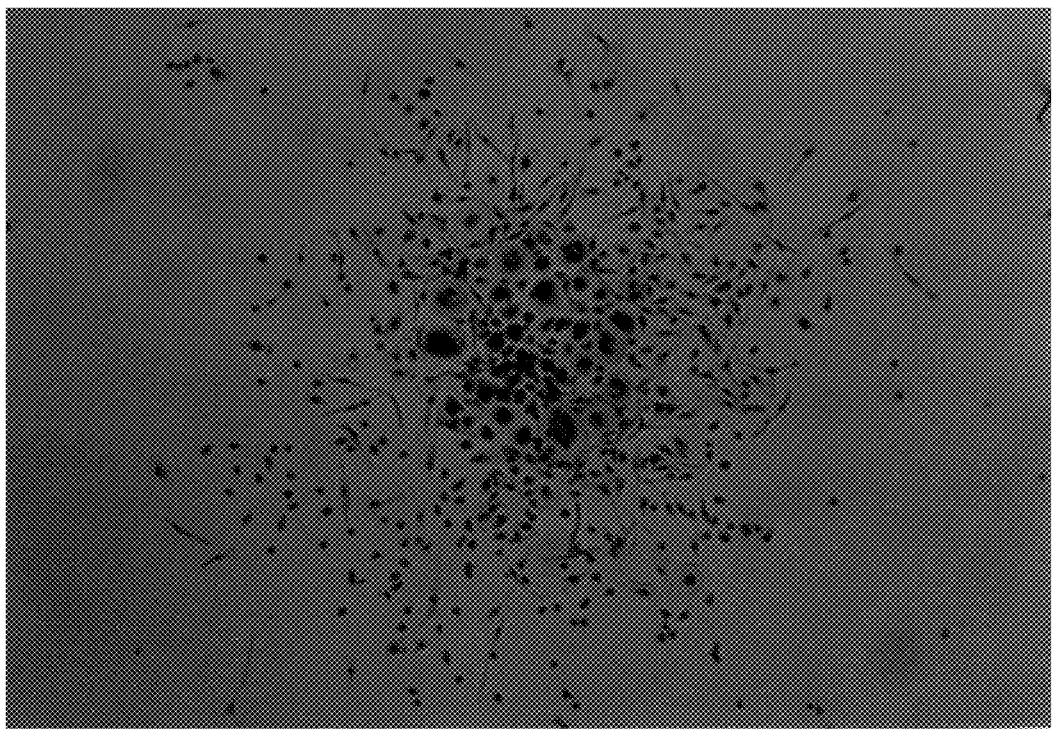
Figure 1C:
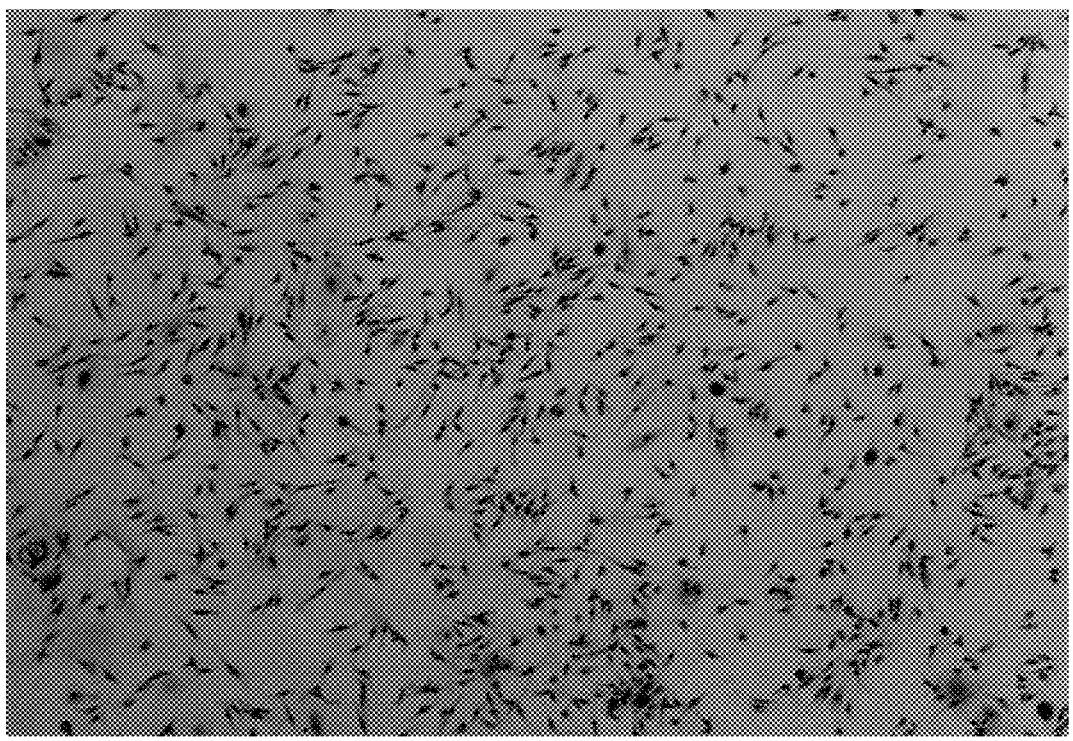

When examined by phase-contrast microscopy, the core of each colony was predominantly formed by several fibroblast-like cells and by few large-flat round cells. Small round cells were also seen, either dispersed within the colonies or on top of the large-flat round cells (FIG. 1B). All cell types forming a colony were weakly positive for Sudan Black and negative for alkaline phosphatase. By day 20 of culture, cells have proliferated and tend to form a near continuous layer comprising mainly fibroblast-like cells. At this time large-flat cells are dispersed and represent only a minor population (FIG. 1C).

As revealed by histochemical analysis (not shown), stromal cells were positive for α-naphthyl butyrate esterase, Periodic Acid Schiff (PAS) and acid phosphatase; weakly positive for Sudan Black and negative for membrane alkaline phosphatase. No significant histochemical differences were observed between fibroblast-like and large-flat round cells.

The immunological characterization of PBPC-derived stromal cells was performed by indirect immunofluorescence, by utilizing a panel of monoclonal antibodies currently used to detect bone marrow stromal cells. The results of these studies are summarized in Table 1.

TABLE 1

Immunofluorescence studies on cultured stromal cells generated from mobilized PBPC harvests.

| | cell type: | |
|---|---|---|
| marker | fibroblast-like | large-flat round |
| fibronectin | +++ | ++* |
| collagen I | ++ | +* |
| collagen III | + | + |
| collagen VI | ++ | + |
| ICAM-1 | +++ | ++ |
| VCAM-1 | ++ | + |
| mesenchymal cells (SH2) | ++ | ++ |
| mesenchymal cells (SH3) | +++ | ++ |
| CD14 | − | − |
| CD34 | − | − |

After in situ staining with the appropriate antibody, cells were scored for positive (*) and negative (−) staining.
*: high expression around nuclei Similarly, micrographs showing selected immunofluorescence stainings (i.e., fibronectin, collagen I, ICAM-1, VCAM-1 and mesenchymal antigen SH-2) are shown in FIG. 2. In general, the staining pattern revealed production of extracellular matrix molecules and expression of adhesion ligands. Together, stromal cells which are CD14− and CD34− express mesenchymal antigens recognized by monoclonal antibodies SH2 and SH3. Without exception, no immunophenotypic differences were observed between fibroblast-like and large-flat round cells.

Small round cells, observed within colonies, proved to be CD45+ and CD34− and were not further analyzed.

Flow cytometry analysis of EDTA-released day-10 stromal cells indicated that more than 85% of cells express unique human mesenchymal stem cell-surface proteins, which were detected by monoclonal antibodies SH-2 and SH-3. (FIG. 3A). Together, the flow cytometric analysis of EDTA-released stromal cells revealed no expression of progenitor or mature hematopoietic cell-associated antigens like, CD34, CD45 and CD14. FIG. 3B shows the pattern of staining of EDTA-released bone marrow stromal cells after labeling with antibodies SH2 and SH3.

Therefore, based on morphology and surface-membrane phenotype, ex vivo generated hMSCs from mobilized hHSC harvests are indistinguishable from bone marrow derived-human mesenchymal stem cells.

Quantitation of hMSCs in HHSC harvests mobilized by growth factors.

The content of hMSCs in growth factor-mobilized hHSC harvests was measured by flow cytometry using monoclonal antibody SH2. $SH2^+$-hMSCs were localized in the higher lymphocyte and in the lower part of the monocyte cell cluster in a forward and side-scatter dot plot. To avoid the scanty overlapping between $SH2^+$ and $CD14^+$ cells and the non-specific binding of the secondary antibody ($IgG_1$) to monocytes, a gate was set around the above zone, to exclude $CD14^+$ cells and to enumerate $SH-2^+/CD14^-$ cells.

$SH2^+$ hMSCs were detected in 11/14 hHSC harvests. The median percentage of $SH2^+$ cells in apheresis products was 0.63% (range 0.02–2.32). No correlation was found between percentage of $SH2^+$ cells or total amount of $SH2^+$ cells per harvest and type of growth factor (GM-CSF or G-CSF) used to mobilize the hHSC harvests.

To establish whether the efficiency of hHSC mobilization (measured as amount of $CD34^+$ cells collected), correlates with amount of $SH2^+$ cells per apheresis, the type of relationship between both variables was analyzed. As seen in FIG. 4, considering the whole group of 14 patients studied, we found a very strong correlation ($r=0.92$, $P<0.001$) between the absolute number of $CD34^+$ cells and that of $SH2^+$ cells, in each apheresis product. These results suggest that the $SH2^+$ number could be predicted from the $CD34^+$ cell number with a high level of confidence.

Mononuclear cells prepared from the blood of three normal donors were negative for $SH2^+$ cells, while mononuclear cells prepared from a blood sample taken to a non-breast cancer patient after 5 days of stimulation with G-CSF, contained 0.11% of $SH2^+$ hMSCs.

DISCUSSION

While in growth factor-mobilized apheresis products the presence of hematopoietic progenitor, as well as that of accessory immune and tumor cells has been well documented.[5,6,18,19,29] No previous information exists, to our knowledge, on the presence of hMSCs in hHSC harvests.

Here we have used a dual approach, which includes the ex vivo generation of hMSCs and their phenotypic characterization, to investigate for the presence of hMSCs in growth factor-mobilized hHSC harvests from breast cancer patients.

Low-density mononuclear cells from hHSC harvests, when cultured in the presence of FCS give rise to a population of strongly adherent cells comprising both isolated and colony-forming fibroblast-like cells, which in the latter case grow together with large-flat round cells. Typical marrow-stroma differentiation markers, such as positivity for Sudan Black and alkaline phosphatase[23], are either weakly expressed or absent in PBPC harvest-derived adherent cells. Early or late myeloid progenitor antigens, like CD34, CD45, CD14, are not expressed by these cells. On the other hand, hHSC harvest-derived hMSCs are recognized by antibodies SH2 and SH3 that react with antigens on the surface of marrow-derived human mesenchymal stem cells, but fail to react with marrow-derived hemopoietic cells.[3] In addition, our studies demonstrate that the phenotypic characteristics of hHSC harvest-derived hMSCs are similar to those of bone marrow derived-hMSCs.

The present invention may be embodied in other specific forms without departing from the spirit or essential character thereof. The embodiments described herein are only illustrative and are not to be considered restrictive. All modifications which come within the meaning and range of the lawful equivalents of the claims are to be embraced within their scope.

CITED REFERENCES

1. Goldman J. Peripheral blood stem cells for allografting. Blood 1995; 85:1413–1415.
2. Schmitz N, Gratwohl A, Goldman J. Allogeneic and autologous transplantation for hematological diseases, solid tumors and immune disorders. Current practice in Europe in 1996 and proposals for an operational classification. BMT 1996; 17:471–477.
3. Richman C M, Winer R S, Yankee Rk Increase in circulating stem cells following chemotherapy in man. Blood 1976; 47:1031–1039.
4. Siena S, Bregni M, Brando B et al. Circulation of $CD34^+$ hematopoietic stem cells in the peripheral blood of high-dose cyclophosphamide-treated patients: enhancement by intravenous recombinant human granulocyte-macrophage colony-stimulating factor. Blood 1989; 74:905–1914.
5. Chao N J, Schriber J R, Grimes K et al. Granulocyte colony-stimulating factor "mobilized" peripheral blood progenitor cells accelerate granulocyte and platelet recovery after high-dose chemotherapy. Blood 1993; 81:2031–2135.
6. Peters W P, Rosner G, Ross M, et al. Comparative effects of granulocyte-macrophage colony-stimulating factor (GM-CSF) and granulocyte colony-stimulating factor (G-CSF) on priming peripheral blood progenitor cells for use with autologous bone marrow after high-dose chemotherapy. Blood 1993; 81: 1709–1719.
7. Sutherland H J, Eaves C J, Lansdorp P M et al. Kinetics of committed and primitive blood progenitor mobilization after chemotherapy and growth factor treatment and their use in autotransplants. Blood 1994; 83: 3808–3814.
8. Mohle R, Haas R, Hunstein W. Expression of adhesion molecules and c-kit on $CD34^+$ hemopoietic progenitor cells: comparison of cytokine-mobilized blood stem cells with normal bone marrow and peripheral blood. J. Hematother. 1993; 2: 483–489.
9. Fernandez M, Minguell J J. Adhesive interactions in the hematopoietic system: regulation by cytokines. Proc Soc Exp Biol Med 1996; 313–323.
10. Orazi A, Cattoretti G, Schiro R et al. Recombinant human interleukin-3 and recombinant human granulocyte-macrophage colony-stimulating factor administered in vivo after high-dose cyclophosphamide cancer chemotherapy: effect on hematopoiesis and microenvironment in human bone marrow. Blood 1992; 79: 2610–2619.
11. Dedhar S, Gaboury L, Galloway P, Eaves C. Human granulocyte-macrophagecolony-stimulating factor is a growth factor active on a variety of cell types of nonhemopoietic origin. Proc Natl Acad Sci(USA) 1988; 85: 9253–9257.
12. Haynesworth S E, Baber M A, Caplan Al. Cell surface antigens on human marrow-derived mesenchymal cells are detected by monoclonal antibodies. Bone 1992; 13: 69–80.
13. Chichester, CO, Fernandez M. Minguell J J. Extracellular matrix gene expression by bone marrow stroma and by marrow fibroblasts. Cell Adhesion Commum 1993, 1: 93–99.
14. Lazarus H M, Haynesworth S E, Gerson S L et al. Ex vivo expansion and subsequent infusion of human bone 14. marrow-derived stromal progenitor cells (mesenchymal progenitor cells): implications for therapeutic use. BMT 1995; 16: 557–564.
15. Haynesworth S E, Baber M A, Caplan Al. Cell surface antigens on human marrow-derived mesenchymal cells are detected by monoclonal antibodies. Bone 1992; 13: 69–80.
16. Simmons P J, Torok-Storb B. Identification of stromal cell precursors in human bone marrow by a novel monoclonal antibody, STRO-1. Blood 1991; 78: 55–62.
17. Brandt J, Srour E F, van Besien K et al. Cytokine-dependent long-term culture of highly enriched precursors of hematopoietic progenitor cells from human bone marrow. J Clin Invest 1990; 86: 932–941.
18. Greenberger J D. The hematopoietic microenvironment. Critic Rev Oncol/Hematol 1991; 11: 65–84.
19. Prockop D J. Marrow stromal cells as stem cells for nonhematopoietic tissues. Science 1997; 276: 71–74.
20. Siena S, Di Nicola M, Bregni M et al. Massive ex vivo generation of functional debdrittic cells from mobilized CD34 blood progenitors for anticancer therapy. Exper. hematol 1995; 23: 1463–1471.
21. Silva M R, Parreira A, Ascensao J L. Natural killer cell number and activity in mobilized peripheral blood stem cell grafts: Conditions for in vitro expansion. Exper Hernatol 1995; 23:1676–1681.
22. Ross A A, Cooper B W, Lazarus H M et al. Detection and viability of tumor cells in peripheral blood stem cell collections from breast cancer patients using immunocytochemical and clonogenic assay techniques. Blood 1993; 82: 2605–2610.
23. Pereira R F, Halford K W, O'Hara M D et at. Cultured adherent cells from marrow can serve as long-lasting precursor cells for bone, cartilage, and lung in irradiated mice. Proc Nati Acad Sci USA 1995; 92:4857–4861.
24. Gronthos S, Greaves S E, Ohta S, Simmons P J. The SRO-L$^+$ fraction of adult human bone marrow contains the osteogenic precursors. Blood 1994; 84: 4164–4173.
25. Galmiche M C, Koteliansky V E, Briere J, et al. Stromal cells from human long term marrow cultures are mesenchymal cells that differentiate following a vascular smooth muscle differentiation pathway. Blood 1993; 82: 66–76.
26. Wilkins B S, Jones D B. Immunohistochemical characterization of intact stromal layers in long-term cultures of human bone marrow. Br J Haematol 1995; 90: 757–766.
27. Verfaille C, Nurley R, Bhatia R et al. Role of bone marrow matrix in normal and abnormal hematopoiesis. Critic Rev Oncol/Hematol 1994; 16: 201–224.
28. Zipori D. Cultured stromal cell lines from hemopoietic tissues. In Tavassoli M (de). Handbook of the hemopoietic microenvironment. Humana Press: Clifton, N.J., 1989, pp 287–329.
29. Leavesley D I, Oliver J M, Svmrt B W, et al. Signals from platelet/endothelial cell adhesion molecule enhance the adhesive activity of the very late antigen-4 integrin of human CD34$^+$ hemopoietic progenitor cell. J Immunol 1994; 153: 4673–4683.
30. Klein G, Muller C A, Tillet E, et al. Collagen type VI in the human bone marrow microenvironment: A strong cytoadhesive component. Blood 1995; 86:1740–1748.
31. Fernandez M, Minguell J J. G-CSF regulates the expression of mRNA for collagen type VI and collagen VI production in human bone marrow stromal cells. Hematology 1997; in press.

What is claimed is:

1. A process for obtaining human mesenchymal stem cells from an individual, comprising:

administering to the individual an effective amount of a growth factor that increases the amount of mesenchymal stem cells in peripheral blood, said growth factor being selected from the group consisting of G-CSF and GM-CSF;

recovering from said individual mesenchymal stem cell enriched peripheral blood; and recovering the mesenchymal stem cells from the mesenchymal stem cell enriched peripheral blood, wherein the human mesenchymal stem cells are SH2+, SH3+, and/or SH4+.

2. The process of claim 1, wherein the mesenchymal stem cells are further CD14– and CD34–.

* * * * *